United States Patent
Pagani et al.

(10) Patent No.: US 6,649,795 B2
(45) Date of Patent: Nov. 18, 2003

(54) PROCESS FOR DECOMPOSING A CARBAMATE AQUEOUS SOLUTION COMING FROM THE UREA RECOVERY SECTION OF A UREA PRODUCTION PLANT

(75) Inventors: Giorgio Pagani, Lugano (CH); Federico Zardi, Breganzona (CH); Domenico Romiti, Lugano (CH)

(73) Assignee: Urea Casale S.A., Lugano-Besso (CH)

( * ) Notice: Subject to any disclaimer, the term of this patent is extended or adjusted under 35 U.S.C. 154(b) by 0 days.

(21) Appl. No.: 10/049,686

(22) PCT Filed: Jun. 15, 2001

(86) PCT No.: PCT/EP01/06775

§ 371 (c)(1),
(2), (4) Date: Feb. 15, 2002

(87) PCT Pub. No.: WO01/96288

PCT Pub. Date: Dec. 20, 2001

(65) Prior Publication Data

US 2003/0013914 A1 Jan. 16, 2003

(30) Foreign Application Priority Data

Jun. 15, 2000 (EP) .............................. 00112688

(51) Int. Cl.⁷ .............................. C07C 273/02
(52) U.S. Cl. .............................. 564/66; 564/70; 564/71
(58) Field of Search .............................. 564/32, 63, 66, 564/67, 72, 70, 71

(56) References Cited

U.S. PATENT DOCUMENTS

| | | | | | |
|---|---|---|---|---|---|
| 3,929,878 A | * | 12/1975 | Mavrovic | ..................... | 564/71 |
| 4,088,684 A | * | 5/1978 | Mavrovic | ..................... | 564/71 |
| 4,110,374 A | * | 8/1978 | Inoue | ........................... | 564/71 |
| 4,540,813 A | * | 9/1985 | van Nassau et al. | .......... | 564/71 |
| 4,801,747 A | * | 1/1989 | Jonckers | ...................... | 564/72 |
| 5,053,538 A | * | 10/1991 | Linton et al. | ................. | 564/70 |
| 5,359,140 A | * | 10/1994 | Granelli et al. | ............... | 564/67 |
| 5,523,482 A | * | 6/1996 | Pagani | ......................... | 564/67 |
| 5,847,208 A | * | 12/1998 | Dente et al. | .................. | 564/67 |
| 5,849,952 A | * | 12/1998 | Carloni et al. | ................ | 564/71 |
| 6,118,023 A | * | 9/2000 | Jonckers et al. | .............. | 564/70 |
| 6,342,632 B1 | * | 1/2002 | Pagani et al. | ................. | 564/70 |

FOREIGN PATENT DOCUMENTS

WO  WO 96 23767 A  8/1996

OTHER PUBLICATIONS

CA:131:131521 abs of EP934927 Aug. 1999.*
CA:131:288416 abs of RD 424062 Aug. 1999.*

* cited by examiner

Primary Examiner—Jean F. Vollano
(74) Attorney, Agent, or Firm—Sughrue Mion, PLLC

(57) ABSTRACT

In a process for decomposing a carbamate aqueous solution coming from a urea recovery section of a urea production plant at a predetermined temperature by indirect heat exchange with a heating fluid having a different predetermined temperature, the temperature difference between said carbamate aqueous solution and said heating fluid is reduced to a value not higher than 70° C.

5 Claims, 2 Drawing Sheets

PROCESS FOR DECOMPOSING A CARBAMATE AQUEOUS SOLUTION COMING FROM THE UREA RECOVERY SECTION OF A UREA PRODUCTION PLANT

This is a National stage entry under 35 U.S.C. §371 of Application No. PCT/EP01/06775 filed Jun. 15, 2001; the disclosure of which is incorporated herein by reference.

TECHNICAL FIELD

In its most general aspect the present invention relates to the production of urea.

Specifically, the present invention relates to a process for decomposing a carbamate aqueous solution coming from the urea recovery section of a urea production plant. The above carbamate aqueous solution is also hereinafter referred to as "recycle carbamate solution".

BACKGROUND ART

In the art, a series of urea production processes are known essentially based on the performance of a conversion reaction in a reaction space or reactor fed with ammonia and carbon dioxide, and of a recover of the unreacted substances contained in the urea solution leaving the reaction space, in particular ammonia, carbon dioxide and carbamate in aqueous solution, which are recycled to the reaction space.

To this purpose, a plant implementing the above process comprises downstream to a reaction space, a carbamate decomposition unit, operating at substantially the same pressure as the reaction space, for subjecting the urea solution leaving the reaction space to a treatment of partial decomposition of the carbamate and partial separation of free ammonia. It is thus obtained a flow comprising ammonia and carbon dioxide in vapor phase, which is recycled to the reaction space and a flow comprising urea and residual carbamate in aqueous solution.

The plant also comprises a urea recovery section for separating the residual carbamate from the urea, obtaining carbamate in aqueous solution, which is recycled to the reaction space.

The carbamate decomposition unit is generally an apparatus comprising a vertical tube bundle. The carbamate decomposition is performed by heating the urea solution flowing downwards as a falling film inside the tubes and in contact with their internal walls, with a heating fluid such as steam flowing outside the tubes. In this way, unreacted ammonia and carbon dioxide are stripped from the urea solution (thermal stripping).

In case of carbon dioxide stripping, the carbamate decomposition is also carried out by means of a gaseous flow comprising carbon dioxide feed flowing upwards inside the tubes.

An improved process for the production of urea, which is disclosed in EP-A-0 796 244, comprises the addition of a partial decomposition step of the carbamate aqueous solution obtained in the urea recovery section and recycled to the reaction space.

In this way, it is possible to remarkably reduce the amount of water recycled to the reaction space, thus permitting to obtain an increase in the conversion yield and in the production capacity of the plant implementing this process.

To this purpose, the plant is provided with a decomposition unit for subjecting at least part of the carbamate solution coming from the urea recovery section (recycle carbamate solution) to a treatment of partial decomposition or stripping, obtaining an additional flow comprising ammonia and carbon dioxide in vapor phase, which is condensed and recycled to the reaction space.

Although advantageous in many aspects, a drawback which is encountered when operating the above decomposition unit is that the decomposition efficiency is unsatisfactory.

According to the studies carry out by the applicant it has been found, not without surprise, that the film of recycled carbamate solution flowing downwards into the tubes bundle is subjected to undesired breakage and detachment from the tube internal walls, in particular at an upper portion thereof. Where this happens, no wetting of the internal wall is achieved.

This causes a low effective thermal exchange between the heating steam and the liquid film of recycled carbamate solution flowing inside the tubes. The stripping efficiency of the decomposition unit of the recycled carbamate solution is thus lower than expected.

Because of that, in order to have acceptable decomposition efficiency, the decomposition unit need to be manufactured with greater dimensions than those theoretically required, with ensuing high investment costs.

DISCLOSURE OF INVENTION

The technical problem underlying the present invention is that of improving the decomposition efficiency of a decomposition unit of a urea production plant delegated to the stripping (decomposition) of a recycle carbamate solution.

To solve the above problem, the basic idea underlying the present invention is that of modifying the prior art processes for decomposing the recycle carbamate solution in such a way to improve the efficiency of the decomposition units delegated to this decomposition, rather than modifying the structure of these units, which would be complex and involve considerable costs.

Based on the above idea, the problem underlying the present invention is solved by a process for decomposing a carbamate aqueous solution coming from the urea recovery section (recycle carbamate solution) according to the annexed claims 1 to 5.

The recycle carbamate solution generally has a water concentration within the ranges of 10% and 70% and has a temperature of from 70° C. to 120° C. at the outlet of the urea recovery section.

Thanks to the present invention a substantial increase of the decomposition efficiency can be obtained since it is possible to control the evaporation of the film of recycle carbamate solution flowing in the tube bundle of the decomposition unit.

In particular, it has been surprisingly found out that the detachment of the film of recycle carbamate solution from the tube walls of prior art units is principally due to the fact that this solution is subjected to an excessive and violent evaporation in the tubes, especially in the upper portion thereof. In other words, it is such unexpected evaporation that disturbs the normal downward flow of the liquid film in the tubes.

In order to effectively hinder these evaporation phenomena, it has been proposed according to the invention to advantageously reduce the high temperature difference between the operating temperature of the heating fluid (e.g. 210° C.) and the temperature of the recycle carbamate solution entering the tubes of the decomposition unit (70–120° C.).

According to the invention, it has been surprisingly found out that if the above temperature difference is not higher than 70° C., preferably between 20° and 40°, the undesired violent evaporation phenomena are substantially eliminated and, at the same time, an increased decomposition efficiency of the decomposition unit is obtained.

This result is totally unexpected if one considers that, in principle, a low temperature difference between the temperature of the recycle carbamate solution and the operating temperature of the heating fluid is expected to reduce the carbamate decomposition into gaseous ammonia and carbon dioxide.

Further characteristics and advantages of the present invention are set forth in the detailed description of a preferred embodiment thereof given below by way of non-limiting example with reference to the annexed drawings.

MODES FOR CARRYING OUT THE INVENTION

Figure 1:
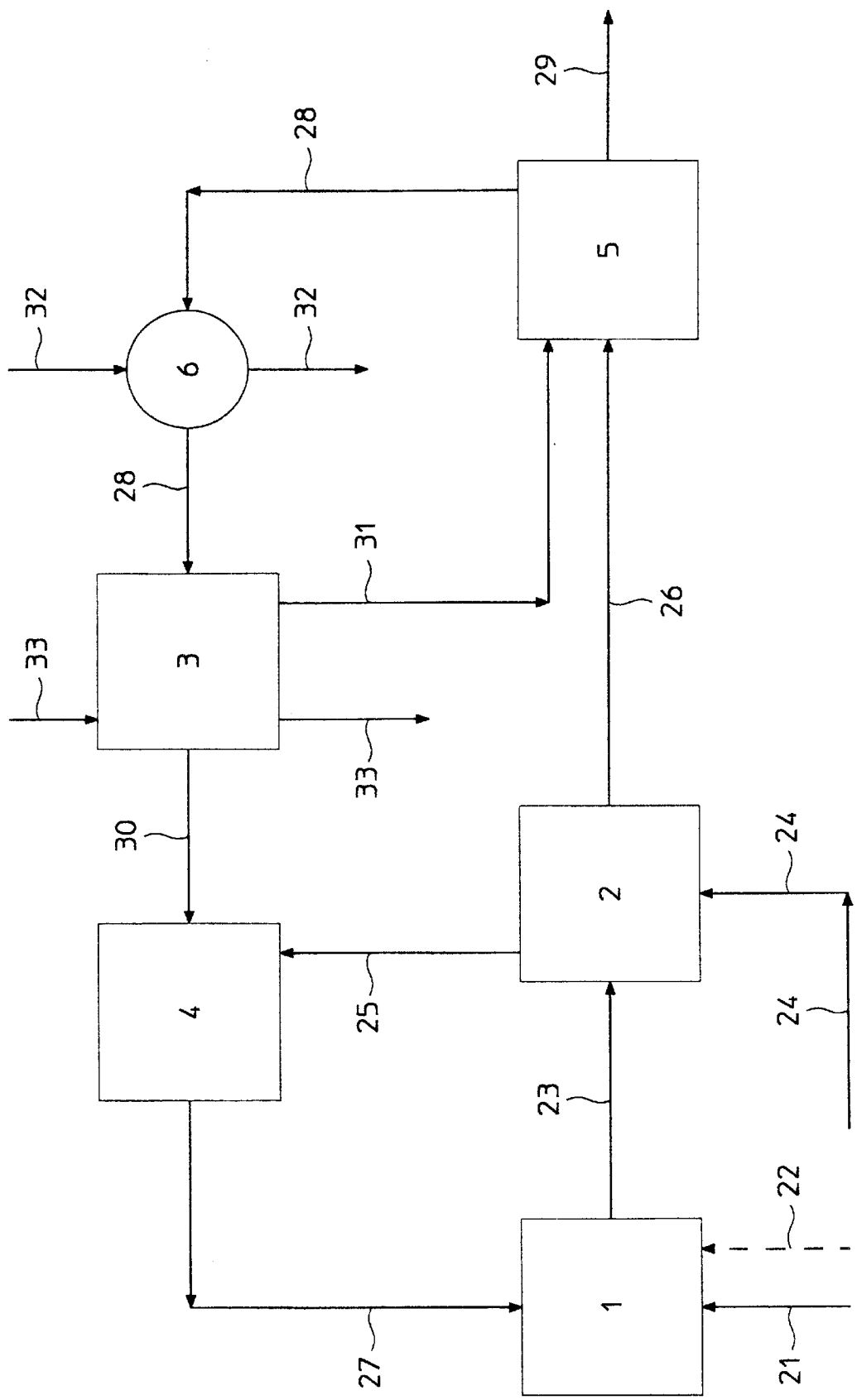
FIG. 1 shows a block diagram schematically illustrating a urea production plant in which the decomposition of the carbamate solution coming from the urea recovery section is achieved according to the invention.

With reference to FIG. 1, block 1 indicates a high-pressure reaction space for the synthesis of urea, which is fed by gas flow 21 comprising substantially pure ammonia.

Blocks 2 and 3 indicate both a high-pressure decomposition unit and block 4 indicate a high-pressure condensation unit.

The decomposition units 2 and 3 and the condensation unit 4 generally operate at substantially the same pressure as in the reaction space 1.

A urea recovery section is indicated as a whole by block 5.

Flow line 23 represents a liquid flow of a reaction mixture coming from block 1 and comprising urea and unreacted substances, notably carbamate and free ammonia in aqueous solution.

The liquid flow 23 is fed to block 2, where it is subjected to a treatment of partial decomposition of the carbamate and partial separation of the free ammonia.

The decomposition unit indicated by block 2 comprises a stripping apparatus, which operates with a gas flow 24 of carbon dioxide feed as stripping agent.

In case the carbamate decomposition in unit 2 is carried out by heat exchange only (thermal stripping), then flow line 24 is missing and a gas flow of carbon dioxide feed is directly fed to the reaction space 1 (see flow line 22 in broken lines).

At the outlet of block 2, flow lines 25 and 26 are shown which represent a gas flow comprising ammonia and carbon dioxide in vapor phase and a liquid flow comprising urea and residual carbamate in aqueous solution, respectively.

Flow line 25 crosses the condensation unit represented by block 4, where ammonia and carbon dioxide in vapor phase are at least partially condensed obtaining a liquid flow of carbamate in aqueous solution and possibly a gaseous flow comprising ammonia and carbon dioxide in vapor phase.

Both flows are then recycled together to the reaction space 1 through the flow line 27.

The flow comprising urea and residual carbamate indicated by the flow line 26 passes through the urea recovery section 5, which is composed by several units and where the residual carbamate is separated from the urea solution, to obtain a additional portion of carbamate in aqueous solution.

Flow line 28 represents the above additional portion of carbamate in aqueous solution at the outlet of the urea recovery section 5. This carbamate solution has generally a content of water of 10% and 70% and a temperature within the range of 70° C. to 120° C.

The urea solution is subjected to a granulation or prilling step in appropriate units of the urea recovery section 5 where melt urea is solidified to a final product leaving the urea production plant through the flow line 29.

According to a preferred embodiment of the present invention, the additional portion of carbamate in aqueous solution leaving block 5 through flow line 28 is advantageously preheated in a heat exchanger indicated by block 6. The so heated carbamate aqueous solution is then subjected to a treatment of partial decomposition in a decomposition unit indicated by block 3 as will be explained in more detail in the following of the description.

Preferably, the above pre-heating of the carbamate solution in block 6 and the thermal decomposition in block 3 is achieved using the heat removed in the condenser (block 4) in the form of steam, to secure minimum energy consumption.

In fact, at least part of this steam crosses, as external heating means, the heat exchanger 6 through the flow line 32 and the decomposition unit 3 through the flow line 33.

At the outlet of block 3, it is then obtained a flow 30 comprising ammonia and carbon dioxide in vapor phase and a flow 31 comprising residual carbamate in aqueous solution.

The flow 30 is at least partially condensed in block 4 to obtain carbamate in aqueous solution, which is recycled to the reaction space 1 through the flow line 27.

The flow 31 comprising residual carbamate in aqueous solution is instead sent to the urea recovery section 5 for further processing.

Figure 2:
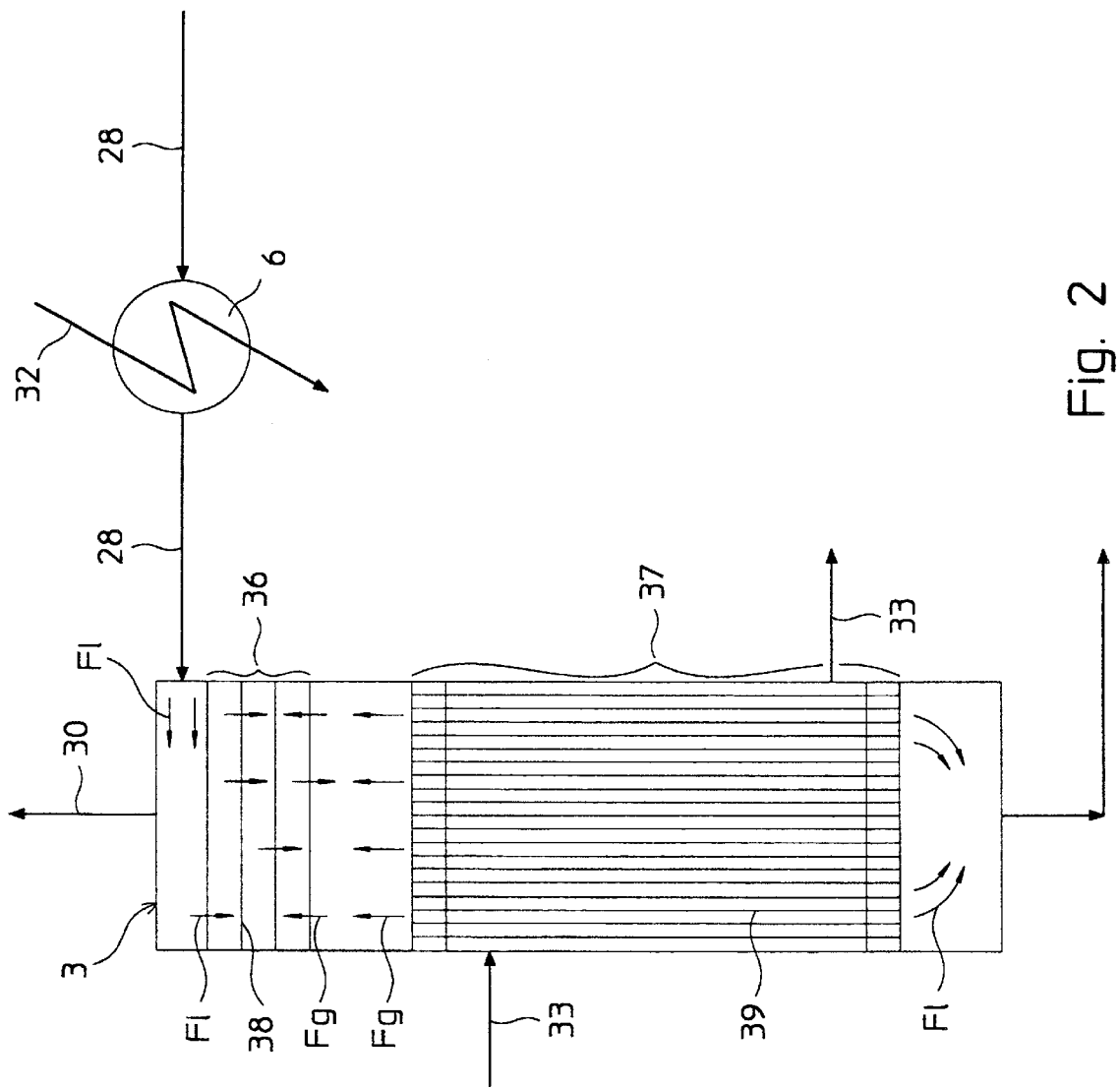
FIG. 2 shows schematically a suitable apparatus for decomposing a recycle carbamate solution according to the present invention.

In FIG. 2, a preferred embodiment of a decomposition unit 3 delegated to decompose the recycle carbamate solution according to the invention is schematically shown.

This decomposition unit 3 has a upper zone 36 comprising a plurality of horizontal perforated plates 38 and a lower stripping zone 37 comprising a tube bundle having a plurality of tubes 39 disposed vertically.

The tubes 39 are externally heated by a flow of a heating fluid such as steam indicated by the flow line 33 and having a temperature for instance of about 210° C.–230° C. The stripping zone 37 thus operates at a temperature comprised within the range of about 170° C. to about 210° C.

According to this embodiment, the recycle carbamate solution represented by the flow line 28, is first partially preheated into the heat exchanger 6 by indirect heat exchange with steam represented by the flow line 32 and then fed into the condensation unit 3 in proximity of its upper end.

In particular, the above recycle carbamate solution has generally a temperature within the range of 70° C. to 120° C. when leaving the urea recovery 5 and is partially preheated in block 6 to a temperature for instance of about 110° C. to 160° C.

The liquid flow 28 of preheated recycle carbamate solution fed in the decomposition unit 3 is made to flow downwards by gravity through the plates 38 of the upper zone 36 in countercurrent with a gaseous flow comprising ammonia and carbon dioxide coming from the stripping zone 37.

In FIG. 2, the flows of the gaseous phase and the liquid phase inside the condensation unit 3 are indicated with reference signs Fg and Fl, respectively.

As a result of this contact, the recycle carbamate solution is further preheated in the upper zone 36, so as to obtain a temperature of the carbamate solution before entering the stripping zone 37 of decomposition unit 3 for instance of about 150° C. to 190° C.

From the upper zone 36, the preheated recycle carbamate solution enter the tubes 39 of the stripping zone 37 and flows downward by gravity as a falling film.

According to the invention, the recycle carbamate solution coming from the upper zone 36 has advantageously a temperature similar to the operating temperature of the heating fluid (flow line 33) so as to have a difference between the above temperatures not higher than 70° C., preferably comprised between 20° C. and 40° C.

In this way, the undesired evaporation phenomena within the tubes 39 have been found to be less intense and uncontrolled than in the prior art processes, especially in the upper portion of the tubes 39.

Thanks to the above controlled evaporation of the liquid film of recycle carbamate solution flowing within the stripping zone 37, such film is continuous and maintained in contact with the internal wall of the tubes 39 thus obtaining a practically homogeneous decomposition of the carbamate along all the tubes length.

The decomposition efficiency of the decomposition unit 3 is therefore improved and a high recover of ammonia and carbon dioxide in vapor phase is achieved.

The decomposition unit 3 schematized in FIG. 2 is only an example of a preferred apparatus that can be used for the decomposition of a recycle carbamate solution according to the present invention.

In the alternative, a decomposition unit can be used without the plates 38 and only comprising the stripping zone 37. In this case, all the preheating step of the recycle carbamate solution is carried out in block 6.

Moreover, in particular circumstances, the heat exchanger of block 6 may be suppressed and the recycle carbamate solution inside the unit 3 is preheated heated in the upper zone 36 of the decomposition unit 3 only.

Finally, the decomposition unit 3 can also be operated with a gas flow of carbon dioxide as stripping agent (not shown).

What is claimed is:

1. Process for decomposing an ammonium carbamate aqueous solution coming from a urea recovery section of a urea production plant at a predetermined temperature by indirect heat exchange with a heating fluid having a different predetermined temperature than the temperature of said ammonium carbamate aqueous solution, comprising the step of reducing the temperature difference between said ammonium carbamate aqueous solution and said heating fluid to a value not higher than 70° C.

2. Process according to claim 1, characterized in that said temperature difference is reduced to a value between 20° C. and 40° C.

3. Process according to claim 1, comprising the steps of:
feeding said ammonium carbamate aqueous solution in a decomposition unit (3) comprising a stripping zone (37);
subjecting the ammonium carbamate aqueous solution to a treatment of at least partial decomposition in said stripping zone (37) by indirect heat exchange with a heating fluid to obtain a flow comprising ammonia and carbon dioxide in vapor phase;
characterized in that said ammonium carbamate aqueous solution is heated prior be subjected to decomposition in said stripping zone (37).

4. Process according to claim 3, characterized in that said ammonium carbamate aqueous solution is heated in a heat exchanger (6) prior to being fed into decomposition unit (3).

5. Process according to claim 3, characterized in that said ammonium carbamate aqueous solution is heated by heat exchange with said flow comprising ammonia and carbon dioxide in vapor phase obtained in said stripping zone (37).

\* \* \* \* \*